United States Patent
Mangiardi

(10) Patent No.: US 8,360,970 B2
(45) Date of Patent: Jan. 29, 2013

(54) SURGICAL ACCESS INSTRUMENTS FOR USE WITH SPINAL OR ORTHOPEDIC SURGERY

(75) Inventor: John R. Mangiardi, Greenwich, CT (US)

(73) Assignee: Vycor Medical, Inc., Boca Raton, FL (US)

( * ) Notice: Subject to any disclaimer, the term of this patent is extended or adjusted under 35 U.S.C. 154(b) by 824 days.

(21) Appl. No.: 11/993,280

(22) PCT Filed: Jun. 22, 2006

(86) PCT No.: PCT/US2006/024243
§ 371 (c)(1),
(2), (4) Date: Jul. 29, 2009

(87) PCT Pub. No.: WO2007/002251
PCT Pub. Date: Jan. 4, 2007

(65) Prior Publication Data
US 2010/0022844 A1    Jan. 28, 2010

Related U.S. Application Data

(60) Provisional application No. 60/692,959, filed on Jun. 22, 2005.

(51) Int. Cl.
*A61B 17/16* (2006.01)
(52) U.S. Cl. ............................ 600/210; 606/99; 606/190
(58) Field of Classification Search .......... 600/201–210; 606/86 R, 90, 96, 99, 105, 190–194
See application file for complete search history.

(56) References Cited

U.S. PATENT DOCUMENTS

| | | | |
|---|---|---|---|
| 2,769,441 | A | 11/1956 | Abramson |
| 2,922,415 | A | 1/1960 | Campagna |
| 3,417,746 | A | 12/1968 | Moore et al. |
| 3,626,471 | A | 12/1971 | Florin |
| 3,766,910 | A | 10/1973 | Lake |
| 3,882,855 | A | 5/1975 | Schulte et al. |
| 3,888,117 | A | 6/1975 | Lewis |
| 4,263,900 | A | 4/1981 | Nicholson |

(Continued)

FOREIGN PATENT DOCUMENTS

| | | |
|---|---|---|
| JP | 05-344978 | 12/1993 |
| JP | 2003-153907 | 5/2003 |

(Continued)

OTHER PUBLICATIONS

Hilton, et al. "METRx Microdiscectomy Surgical Technique," Medtronic Sofamor Danek publication, 2001, 20 pages.

(Continued)

*Primary Examiner* — Alvin Stewart
*Assistant Examiner* — Tara Carter
(74) *Attorney, Agent, or Firm* — RatnerPrestia

(57) ABSTRACT

A surgical access assembly is provided for retaining tissue, membrane, and organs in a retracted position after insertion into an incision on a patient. The assembly includes a hollow surgical access channel of oblong cross-section optionally expandable and contractible in diameter, thereby providing means for distraction of structure affixed to the retractor. The assembly optionally further comprises: gripping means for grasping by a surgeon or device and an introducer of generally oblong cross-section. The introducer, adapted to fit within the access channel, is generally rectangular in cross-section, rounded at the edges, with parallel sides. The distal end of the introducer protrudes from the retractor when inserted therein, and works to delicately push tissue apart. The introducer is placed within the hollow access channel and provides an hollow access channel for access by a surgeon and surgical instruments.

24 Claims, 8 Drawing Sheets

U.S. PATENT DOCUMENTS

| | | | |
|---|---|---|---|
| 4,312,353 | A | 1/1982 | Shahbabian |
| 4,502,468 | A | 3/1985 | Burgin |
| 4,636,199 | A | 1/1987 | Victor |
| 4,931,039 | A | 6/1990 | Coe et al. |
| 4,945,896 | A | 8/1990 | Gade |
| 5,052,373 | A | 10/1991 | Michelson |
| 5,135,526 | A | 8/1992 | Zinnanti et al. |
| 5,160,323 | A | 11/1992 | Andrew |
| 5,249,568 | A | 10/1993 | Brefka et al. |
| 5,275,583 | A | 1/1994 | Crainich |
| D377,093 | S | 12/1996 | Michelson |
| 5,782,807 | A | 7/1998 | Falvai et al. |
| 5,785,648 | A | 7/1998 | Min |
| 6,093,145 | A | 7/2000 | Vom Berg et al. |
| 6,096,038 | A | 8/2000 | Michelson |
| 6,142,931 | A | 11/2000 | Kaji |
| 6,156,054 | A | 12/2000 | Zadno-Azizi et al. |
| 6,221,078 | B1 | 4/2001 | Bylsma |
| 6,224,599 | B1 | 5/2001 | Baynham et al. |
| 6,296,647 | B1 | 10/2001 | Robioneck et al. |
| 6,371,964 | B1 | 4/2002 | Vargas et al. |
| 6,383,191 | B1 * | 5/2002 | Zdeblick et al. ............ 606/105 |
| 6,425,859 | B1 | 7/2002 | Foley et al. |
| 6,565,574 | B2 | 5/2003 | Michelson |
| 6,589,211 | B1 | 7/2003 | MacLeod |
| 6,595,917 | B2 | 7/2003 | Nieto |
| 6,599,292 | B1 * | 7/2003 | Ray ............................ 606/90 |
| 6,761,687 | B1 | 7/2004 | Doshi et al. |
| D495,053 | S | 8/2004 | Laun |
| 6,863,674 | B2 | 3/2005 | Kasahara et al. |
| 6,896,680 | B2 | 5/2005 | Michelson |
| 7,081,089 | B2 | 7/2006 | Bonadio et al. |
| 7,153,304 | B2 | 12/2006 | Robie et al. |
| 7,235,084 | B2 | 6/2007 | Skakoon et al. |
| 7,474,820 | B2 | 1/2009 | Vayser et al. |
| 7,510,524 | B2 | 3/2009 | Vayser et al. |
| 7,686,492 | B2 | 3/2010 | Vayser et al. |
| 2001/0010002 | A1 | 7/2001 | Michelson |
| 2002/0151769 | A1 | 10/2002 | Kim |
| 2002/0161366 | A1 | 10/2002 | Robie et al. |
| 2004/0097792 | A1 | 5/2004 | Moll et al. |
| 2004/0230100 | A1 * | 11/2004 | Shluzas ...................... 600/208 |
| 2005/0273132 | A1 * | 12/2005 | Shluzas et al. ............. 606/198 |
| 2005/0277811 | A1 | 12/2005 | Richards et al. |
| 2006/0122462 | A1 | 6/2006 | Roth et al. |
| 2008/0109026 | A1 | 5/2008 | Kassam |

FOREIGN PATENT DOCUMENTS

| | | |
|---|---|---|
| RU | 45928 | 6/2005 |
| RU | 55570 | 8/2006 |
| SU | 131027 | 11/1959 |
| SU | 349136 | 8/1972 |
| SU | 585840 | 12/1977 |
| SU | 1521465 | 11/1989 |

OTHER PUBLICATIONS

Kelly, et al. "The stereotaxic retractor in computer-assisted stereotaxic microsurgery," Journal of Neurosurgery, vol. 69, Aug. 1988, pp. 301-307, 7 pages.

Alexander, et al. "Chapter 20: Stereotactic Frame Systems: The COMPASS System," Advanced Neurosurgical Navigation, 1999, pp. 267-277. 13 pages.

Engh, et al. NeuroendoportSM surgery facilitates removal of hard-to-reach brain tumors,University of Pittsburgh Neurosurgery News, vol. 10, No. 2, 2009. 8 pages.

Raza,et al. "Minimally Invasive Trans-Portal Resection of Deep Intracranial Lesions," Minimally Invasive Neurosurgery, vol. 54, Feb. 2011, pp. 1-7.

Recinos, et al. "Use of a minimally invasive tubular retraction system for deep-seated tumors in pediatric patients," Journal of Neurosurgery: Pediatrics, vol. 7, May 2011, pp. 516-521. 6 pages.

Prevedello, et al. "Vycor ViewSite TC: Endoscope guided Intraparenchimal Brain Tumor Ressection," Ohio State University Medical Center Minimally Invasive Neurosurgery, 2 pages.

Shults, et al. "Neuro-Opthalmic Complications of Intracranial Catheters," Neurosurgery, vol. 33, No. 1, Jul. 1993, pp. 135-138. 4 pages.

Greenfield, et al. "Stereotactic Minimally Invasive Tubular Retractor System for Deep Brain Lesions," Operative Neurosurgery 2, vol. 63, Oct. 2008, pp. 334-340. 7 pages.

* cited by examiner

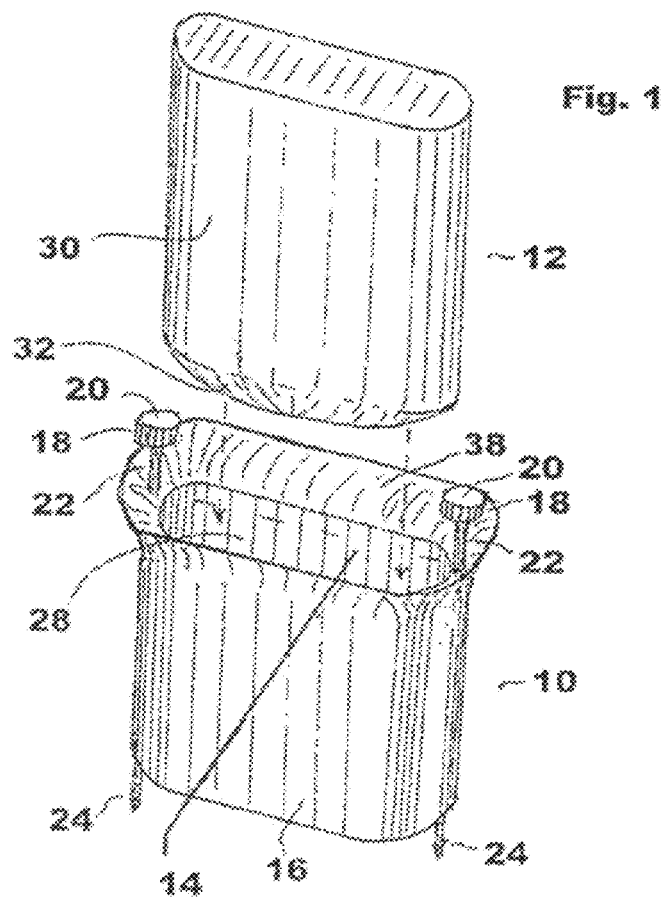
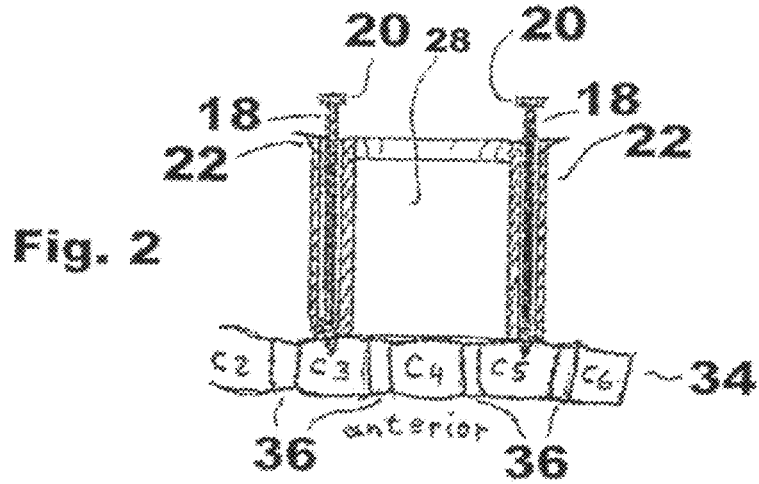

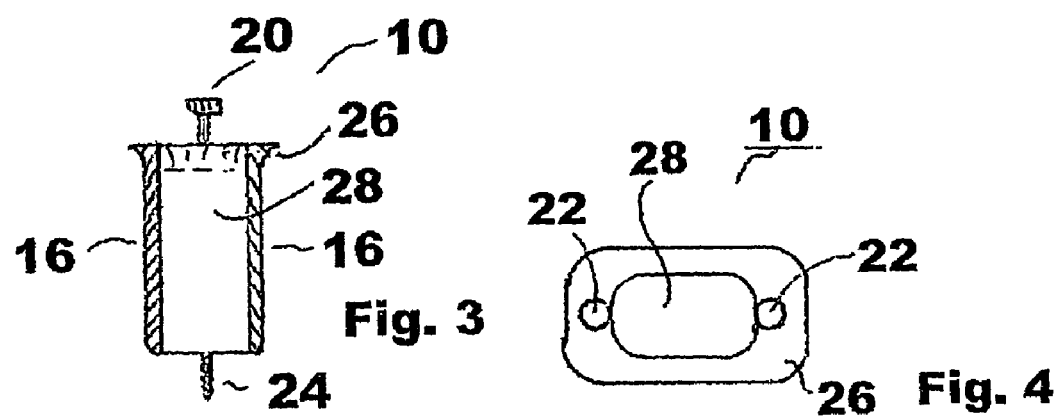
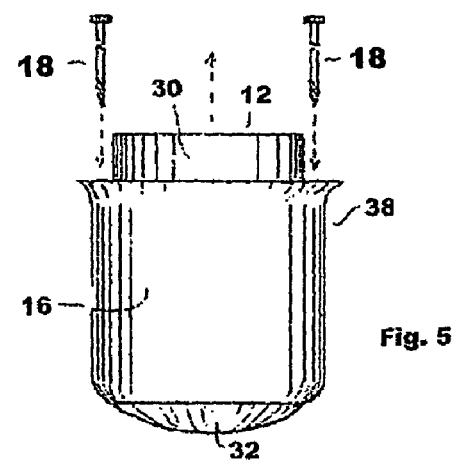

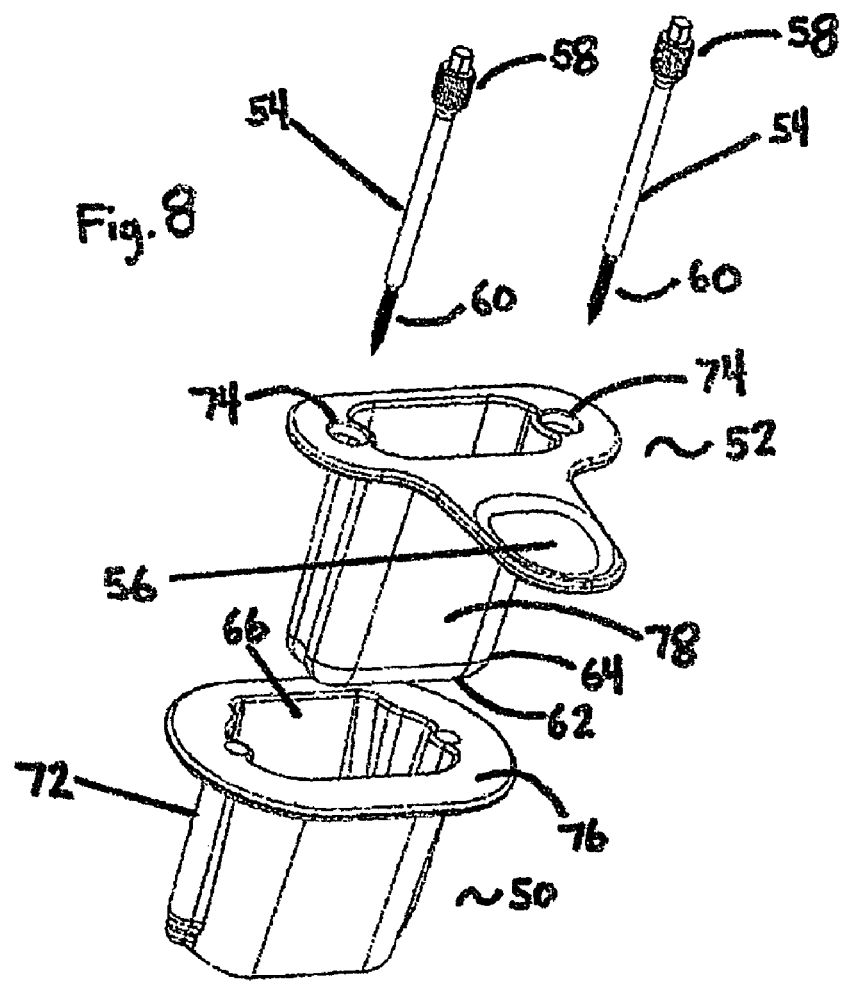
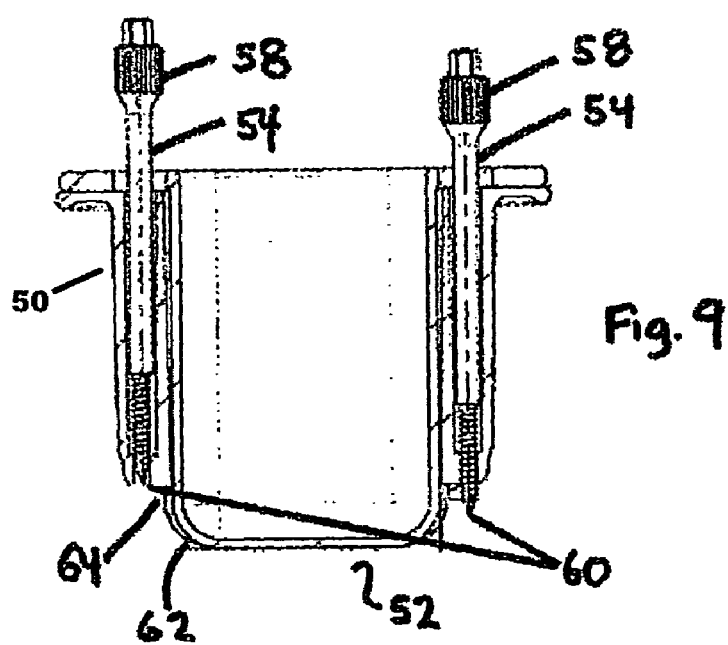

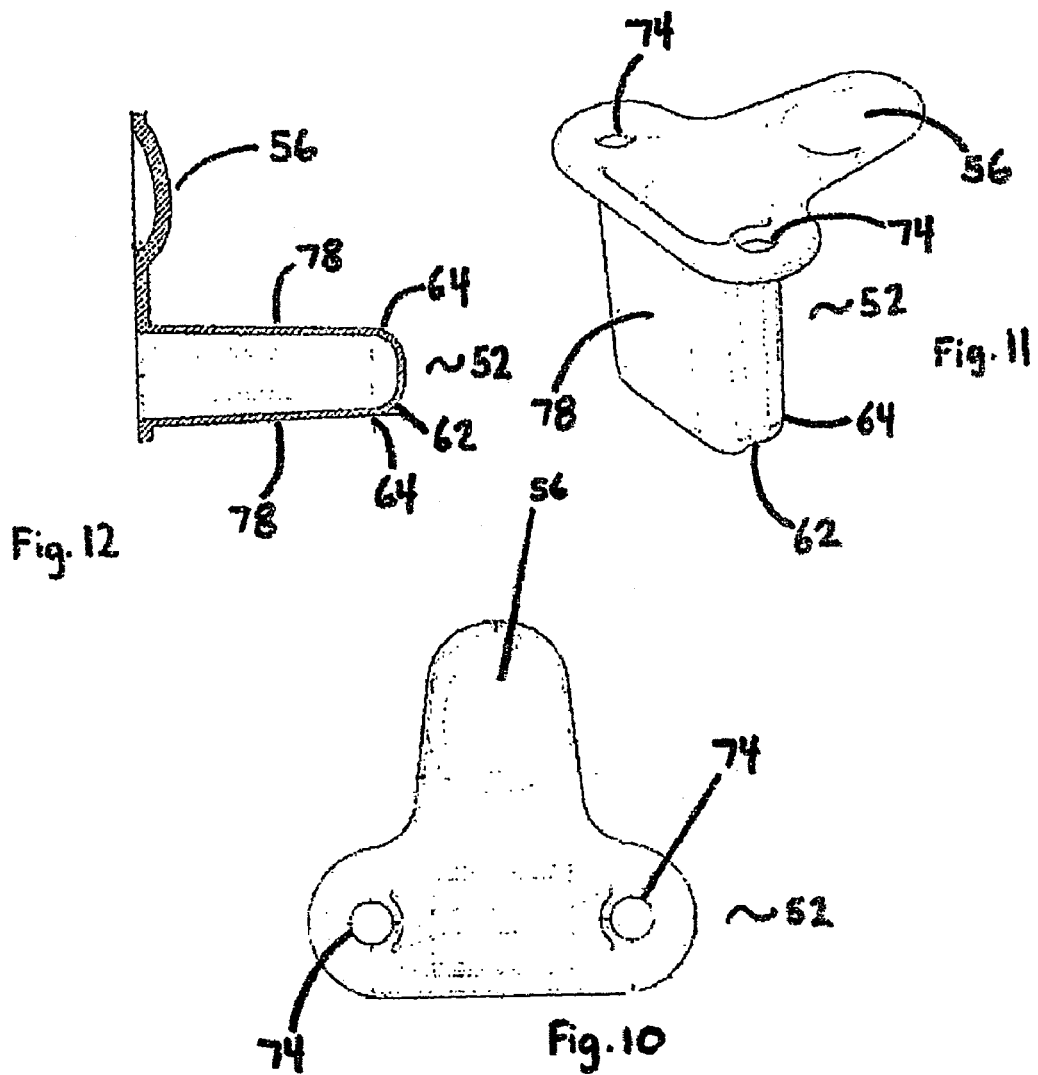

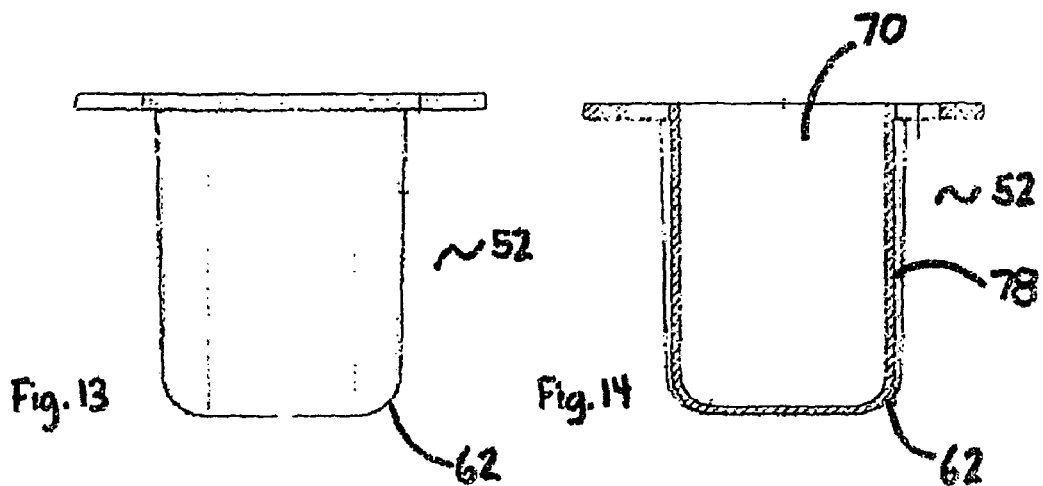
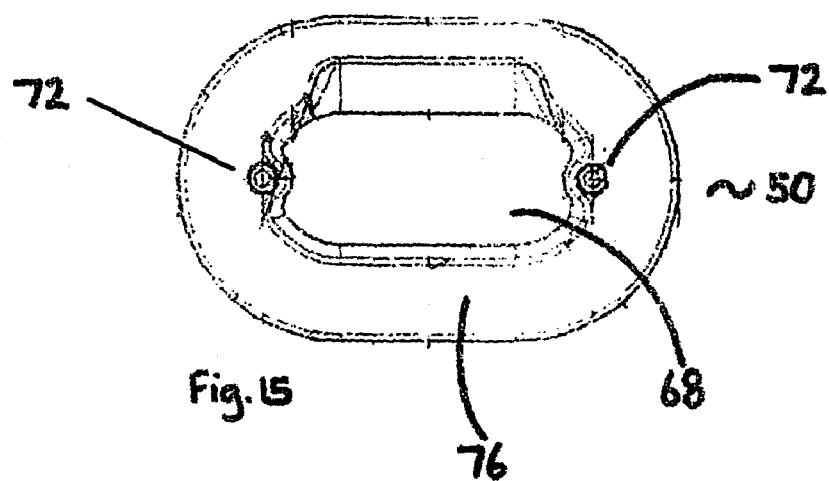

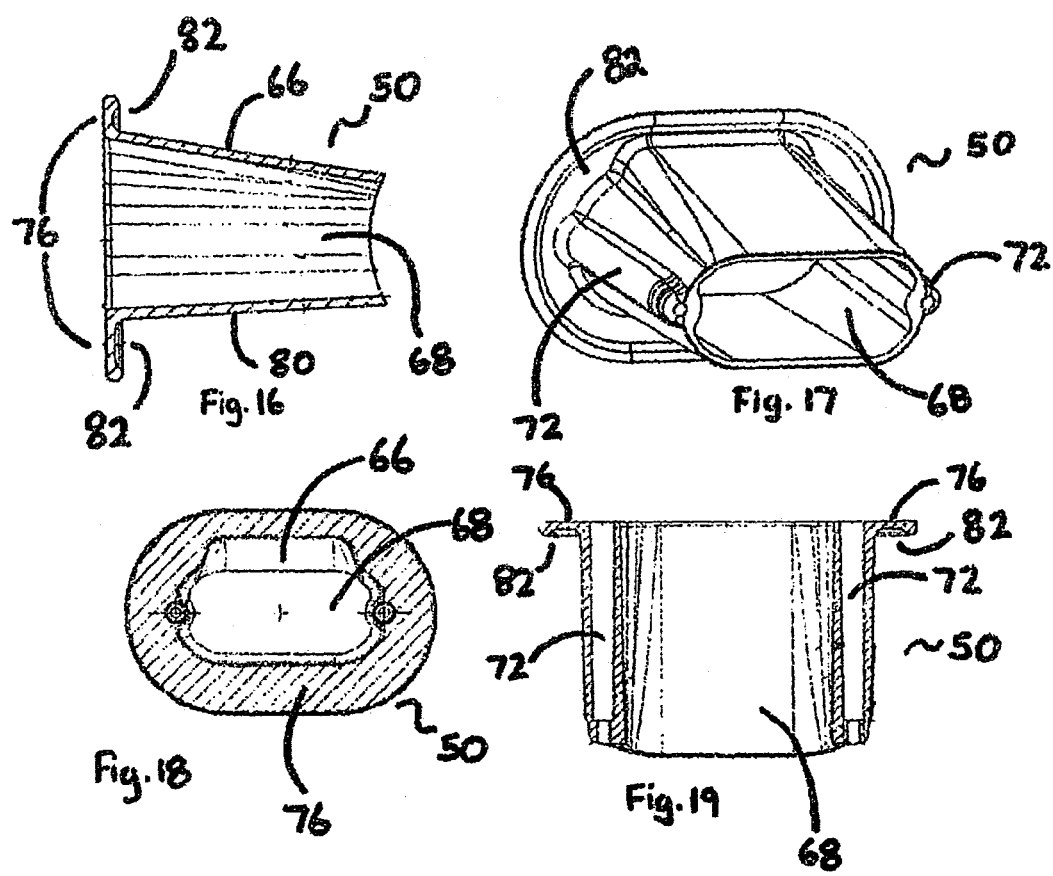

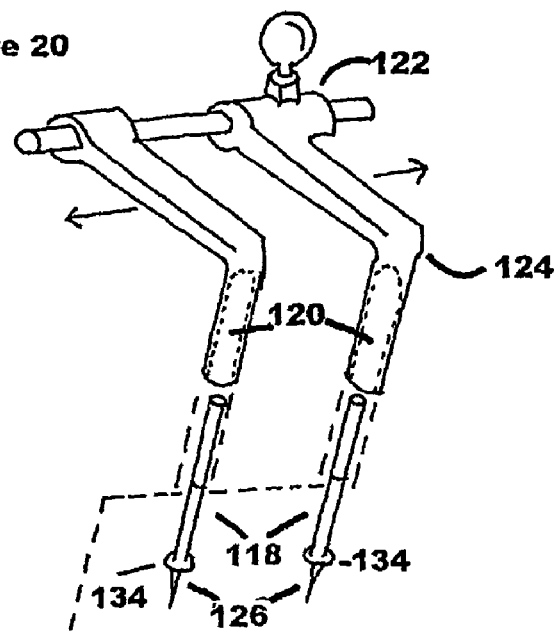
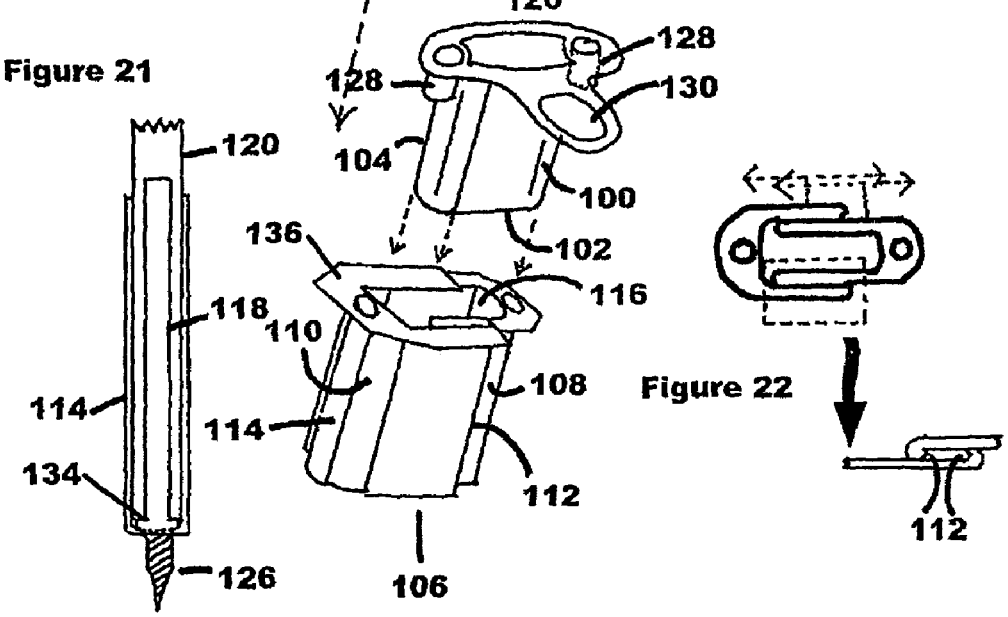

SURGICAL ACCESS INSTRUMENTS FOR USE WITH SPINAL OR ORTHOPEDIC SURGERY

CROSS REFERENCE OF APPLICATION

This application claims the benefit of priority PCT/US06/024243 filed on Jun. 22, 2006 and from U.S. Provisional Application No. 60/692,959, filed on Jun. 22, 2005, the contents of all of which are incorporated herein by reference.

BACKGROUND OF THE INVENTION

1. Field of Invention

The invention relates to surgical access instruments for use with anterior approach spinal surgery, such as anterior spinal fusion surgery associated with herniated discs and other pathology of the cervical spine, and also for use with other orthopedic surgeries.

2. Background of the Invention

Surgery on structures within a patient often requires the use of retracting devices to hold tissues away from the desired surgical site. Many varieties of surgical retractors exist including devices using tubular probes, using paddle-like extensions, or more complicated mechanical assemblies. Probes and even paddle-like extensions exhibit areas of increased, localized retraction pressure, which can result in tissue damage. Further, with paddle-like, wall-like, and especially tubular-shaped probe retractors, tissue intrudes from non-retracted sides.

Typical retractors are usually not affixed into place relative to bone or other structure. While there has been some progress in designing retractors with the capability of being affixed to bone, such as U.S. Pat. No. 5,027,793 to Engelhardt or U.S. Pat. No. 7,014,608 to Larson, these devices are limited in function and use. The Engelhardt device contemplates the use of spikes, driven into bone, and requires the use of multiple retractors and resection with concomitant trauma to overlying and surrounding tissue.

The Larson device requires the surgeon to first locate, after dissection of the underlying tissue, suitable pedicles on vertebrae for the attachment of guideposts. The guideposts are then attached using an awl or other probe to punch a hole followed by insertion of a screw. The Larson retractor is inserted along these guideposts after which the retaining walls are expanded using a separate expanding device to provide a working area The Larson retractor does not provide means for distraction of underlying, affixed bone. Further, the Larson device retracts from a fully closed state to an open state, using hinges, after introduction of a wedge expander. Expansion while affixed to structure can result in accidental damage to affixed structure from mistranslation of the applied expansion force intended for, as in the Larson device, the mechanically coupled tissue retaining walls. A device that provides retraction prior to insertion of fixation means into bone would be of advantage. A surgeon can more easily locate appropriate fixation sites with such a device and the risk of damage to critical areas such as the spine because of mistranslation of the retraction force would be eliminated.

Other traditional cervical retractors include cylindrical retractors as disclosed in U.S. Pat. No. 6,096,038 of Michelson, conical retractors as disclosed in U.S. Pat. No. 6,896,680 of Michelson or rectangular frame strictures as in U.S. Pat. No. 5,052,373 of Michelson. The devices in these patents are designed for localized use and do not generally separate interfering tissues in the body, such as stemomastoid muscles, nerve, carotid artery, esophagus, or trachea of the neck. Further, as in U.S. Pat. No. 5,052,373 of Michelson, the retraction means utilizes jagged edges to grasp surrounding tissue to prevent expulsion of the retractor. Such means can result in surrounding tissue insult. The combination of factors including interfering tissues in the area of the cervical, thoracic or lumbar spine, and the effects of sharp, blunt edges and limited surface area of traditional retractors also results in limited visualization of surgical sites.

Further, there are no presently known access assemblies that can provide both a means for retraction of tissue and distraction of underlying structure. While distraction devices such as the distractor in U.S. Pat. No. 5,059,194 of Michelson are known. These devices require a separate retraction means. The placement of traditional distractors within the retractor channel occludes the surgeon's view and requires additional intrusions into patient tissue for the separate fixation of the distractor. A device that can function both as a distractor and as a retractor would eliminate the need for separate screws into the vertebral body and would maximize the available space for other surgical instruments. A device such as this would be of benefit.

The present surgical access assembly safely addresses the shortcomings of the presently known instruments. In keeping with the present invention, the objects and design principles of the surgical access assembly of this invention are as follows:

1) to maximize surface area of the retractor, so as to distribute pressure evenly and minimize effective local retraction pressure;
2) to provide a retraction device that allows for prevention of tissue "creep" around the edges of the retractor.
3) to provide a surgical access assembly that can be firmly and safely fixed to the underlying bone so as to obviate tissue intrusion around the working edges of the retractor.
4) to reduce the possibility of accidental over-retraction and thereby avoid carotid, recurrent laryngeal nerve, esophageal and or tracheal damage, in the cervical spine, and to avoid other surrounding tissue insult elsewhere;
5) to allow for binocular vision with the utilization of oblong architecture;
6) to allow for maximal access of light to target tissue, aiding in visualization of said target tissue;
7) to allow for minimization of skin and tissue disruption with the utilization of tapered forward edges or a flange and capture perimeter which spans forward of the incision area;
8) to enable stable retraction fixation to avoid accidental retractor displacement and minimize injury to surrounding structures;
9) to provide retractors which are of lightweight, biocompatible materials to allow for ease of manipulation and safety;
10) to provide transparent retractors to allow for improved visualization of surrounding structures;
11) to provide a retractor which has an adjustable size, particularly an adjustable access channel diameter;
12) to provide a retractor which can affix into bone or tissue and function to distract segments of affixed bone or tissue; and/or,
13) other objects that become apparent from the following descriptions and discussion of the present invention.

One or more of the above objects is met in whole or in part by the various embodiments of this invention.

SUMMARY OF THE INVENTION

The invention is a surgical device which comprises a retractor and an introducer, said device optionally compatible with a standard distractor device, and which can provide a hollow surgical access channel for surgical instruments, fixable to vertebrae or other bone. In a typical use, the introducer is placed within the hollow surgical access channel of the retractor. The assembly is then placed into an incision on a patient, the protruding distal tip of the introducer working to delicately push tissue and structure away and along the smooth walls of the retractor. When fully inserted, the retractor may be stably affixed to bone, and the introducer removed. The retractor and its hollow surgical access chamber then provides improved access for surgical instruments, and the retractor, with minimal localized retraction pressure, ensures surrounding tissue is displaced.

In an alternative embodiment, the introducer and retractor assembly is inserted into the patient as before and affixed to vertebrae. Surgical access is provided to the disc space between vertebrae when a distractor, a device capable of pushing apart structure, is attached to the fixation means attached to the retractor and the underlying bone, and the distractor actuated. For example, a screw, placed through a fixation shaft on the retractor, is affixed to one vertebra. A second screw, also placed through a fixation shaft on the retractor, is affixed to an adjacent vertebra. The distractor is attached to each of these screws as well, and when the distractor is actuated, the vertebrae are pulled apart. Access is thereby provided to the disc space. Upon completion of the surgery, the distractor is actuated to relieve its distraction pressure, and the assembly is removed from the patient.

BRIEF DESCRIPTION OF THE DRAWINGS

The present invention can best be understood in connection with the accompanying drawings. The invention is not limited to the precise embodiments shown in drawings, in which:

FIGS. 1 through 5 comprise views of an embodiment of the invention; wherein, FIG. 1 is a perspective view of the introducer positioned over the retractor of this invention;

FIG. 2 is a side cross-section view of the retractor of this invention positioned over a section of cervical vertebrae that are shown schematically;

FIG. 3 is an end cross-section view of the retractor;

FIG. 4 is a top plan view thereof; and

FIG. 5 is a side elevation of the retractor of this invention with the introducer positioned within the access channel prior to insertion at the surgical site.

FIGS. 6 through 19 comprise views of an additional embodiment of the invention; wherein, FIG. 6 is a top plan view of the introducer and retractor with the introducer positioned within the access channel prior to insertion at the surgical site;

FIG. 7 is a side cross-section view of the introducer with the introducer positioned within the access channel prior to insertion at the surgical site;

FIG. 8 is a perspective view of the introducer positioned over the retractor of this invention with a possible fixture means, namely screws, positioned over the vertical fixation shafts;

FIG. 9 is a side cross-section view of the introducer with the introducer positioned within the access channel and a possible fixation means, namely screws, positioned partially within the vertical fixation shafts and fully within the vertical fixation shafts;

FIG. 10 is a top plan view of the introducer only;

FIG. 11 is a perspective view of the introducer only;

FIG. 12 is a side cross-section view of the introducer only;

FIG. 13 is a side view of the introducer only;

FIG. 14 is another side cross-section view of the introducer only;

FIG. 15 is a top plan view of the retractor only;

FIG. 16 is a side cross-section view of the retractor only;

FIG. 17 is a perspective view of the retractor only;

FIG. 18 is a top-plan view of the retractor only; and

FIG. 19 is a side cross-section view of the retractor only;

FIGS. 20 through 22 comprise views of an alternative embodiment of the invention; wherein, FIG. 20 is a perspective view of the distractor and introducer positioned over the retractor;

FIG. 21 is an exploded view of the fixation means fully chambered within the vertical fixation shaft and the distractor shaft fully chambered within the vertical fixation shaft and over the fixation means.

FIG. 22 is a top-plan cross-section view of the retractor, the flange and capture edge not shown, showing the interlocking halves of the retractor and their range of motion. A detail view indicates a possible means for incorporation of a clasping edge.

BRIEF DESCRIPTION OF REFERENCE NUMERALS

FIGS. 1-5

Figure 6:
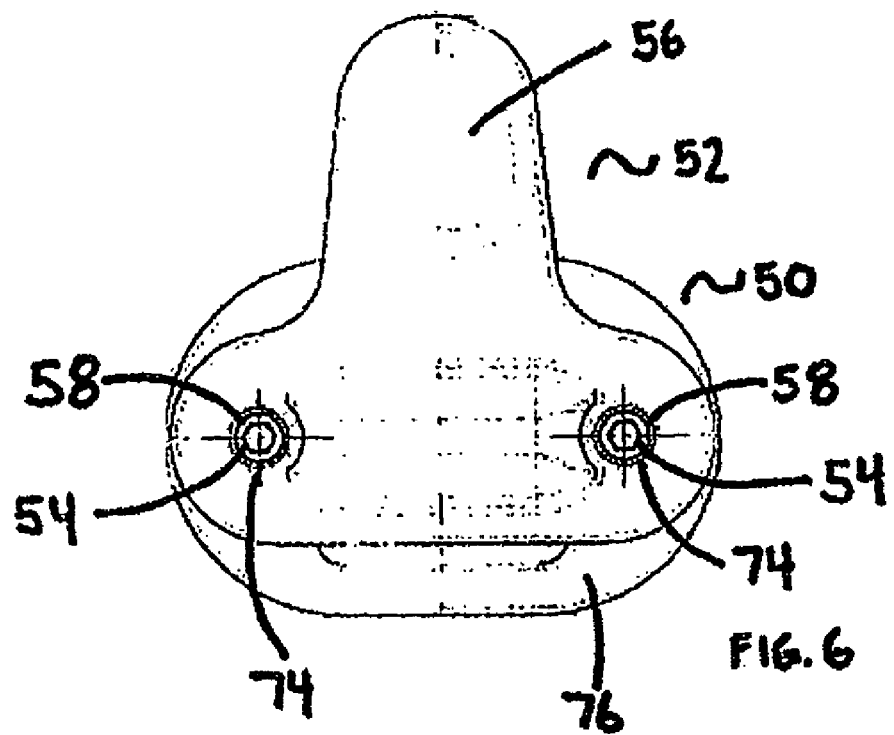

10 Retractor; 12 Introducer; 14 Parallel Wall; 16 Parallel Wall (Retractor); 18 Fixation Means (Screws); 20 Screw Heads; 22 Vertical Fixation Shafts; 24 Pointed Screw Ends; 26 Proximal Edge; 28 Hollow Surgical Access channel; 30 Parallel Wall (Introducer); 32 Distal End of Introducer; 34 Vertebrae; 36 Discs; 38 Tapered Edge

FIGS. 6-19

50 Retractor; 52 Introducer; 54 Fixation Means (Screw); 56 Gripping Means (Thumb-Grip); 58 Screw Head; 60 Screw Tip; 62 Protruding Distal End (Introducer); 64 Junction Point to Retractor (Introducer); 66 Tapered Wall (Retractor); 68 Hollow Surgical Access Chamber (Retractor); 70 Hollow, Terminus-Barriered Introducer Chamber (Introducer); 72 Vertical Fixation Shafts (Retractor); 74 Vertical Fixation Shaft Entryway (Introducer); 76 Flange Surface (Retractor); 78 Introducer Walls; 80 Straight Wall (Retractor); 82 Capture Perimeter

FIGS. 20-22

100 Introducer Wall; 102 Introducer Distal Protruding End; 104 Introducer; 106 Retractor; 108 Retractor First Half; 110 Retractor Second Half; 112 Clasping Edge; 114 Vertical Fixation Shafts; 116 Surgical Access Chamber; 118 Fixation Means (Screw); 120 Fixation Means Channel (Screw Head Channel); 122 Distractor Expansion/Contraction Means; 124 Distractor; 126 Screw Head; 128 Extruded (Sleeved) Introducer Channel and Retractor Retainer; 130 Thumb-Grip; 132 Capture Perimeter; 134 Screw Ring; 136 Flange Surface

DETAILED DESCRIPTION OF THE INVENTION

This disclosure relates to a surgical access assembly and system for use with cervical and lumbar vertebrae and discs and methods of using the surgical access assembly. The surgical access assembly is designed for use during spinal surgery, although it may be used in any medical context.

The surgical access assembly can include:
1) a retractor comprising: a single piece construction in the shape of an extruded "O", thereby providing an oblong cross-section; a two piece construction, each piece in the shape of an extruded "U", thereby providing an oblong cross-section when interlocked. The latter embodiment is optionally expandable, contractible, or both, said expansion or contraction occurring generally along the axis substantially defined by the line parallel to the plane defined by the top of the retractor and substantially intersecting the fixation points. Both embodiments of retractor are adapted to provide a hollow surgical access channel;

2) a rounded introducer of oblong cross-section;

3) vertebral or osteopathic fixations shafts or entryways placed at opposite walls of the retractor, the introducer, or both, said fixation shafts adapted to receiving a fixating device such as a screw. Optionally, the shaft of the retractor is positioned to receive a fixating device that passes through an entryway or interleaving shaft from the introducer, providing stability during introduction of the apparatus in a patient. Further, the shaft receives a fixating device for fixation into vertebrae or other osteopathic structures above and below the surgical area near the disc or other structure to be operated on;

4) a distractor device which can be used to expand or contract the cross-sectional diameter of the retractor and can therefore be used to aid in the separation of tissue or structure such as vertebrae;

5) gripping means for use by the surgeon in aiding the positioning and introduction of the assembly, such as a thumb-grip.

These assembly portions are formed to maximize the surface area of the retractor, which distributes pressure approximately equally though out the surrounding tissues and minimizes effective localized retraction pressure on the tissues in contact or immediately surrounding the retractor, such as the esophagus, the carotid artery, the trachea, nerves, or sternomastoid muscle. Further, the retractor is designed such that the proximal edges are either flared or comprise a top flange from which the hollow access channel is extruded. Said flare and flange minimizes tissue and skin disruption and also prevents tissue creep over the edges of the top of the retractor.

The dimensions of the surgical access assembly may vary and be modified according to an intended use. Generally, the surgical workspace formed by the introducer portion can have diameters in the range of approximately 2.5 cm, although this width can be varied. The top to bottom height varies, depending upon the spinal surgical site. Additionally, the depth is dependent upon the anatomy of the patient. The depth is normally the distance from the outer skin to the anterior surface of the vertebrae in question. Cervical retractors require less depth than abdominal lumbar retractors.

The open configuration may also be determined by the overall desired circumference and diameter of the surgical access assembly for a particular use and may be manufactured in a variety of useful sizes to be available as is practical or the open configuration may be variable, as in an embodiment of the invention in which the retractor access channel diameter can be varied by use of expansion or contraction means. Further, the embodiment of said retractor with expansion and contraction means allows the introduction of a distractor device over the fixation means and into the fixation shafts, thereby not only allowing expansion and contraction of the shaft diameter but also distraction of tissue such as vertebrae, thereby allowing access to interstitial tissues such as the disc space for removal of disc and ligament.

The surgical access assembly may be formed of any biocompatible material that will provide sufficient stability and strength necessary to provide a surgical work area. The biocompatible material may be disposable or sterilizable for repeated use. In any one embodiment, the surgical access assembly may be formed of a lightweight plastic material for ease of manipulation and/or the material may be transparent to allow improved visualization of underlying tissue or structure. Further, the instrument assembly may be partially composed of shape "memory" materials in which the shape and contours of the structure can be adapted to surrounding patient tissue or structure.

The surgical access assembly is also adapted to eliminate the need to "pull" on a retractor portion to clearly visualize the surgical area by initially providing a sufficient work area via the channel retractor. The use of the hollow surgical access channel portion of the surgical access assembly eliminates or greatly lowers the possibility of accidental over-retraction. By avoiding excess retraction, damage to the surrounding tissues is also avoided, including possible spinal damage.

The preferably oblong rectangular shaped architecture of the surgical access assembly portions is such that medical staff is afforded binocular vision, rather than the monocular vision typically found in similar devices. This oblong architecture also provides far greater clearance for lighting access to illuminate the target surgical area and allow full visualization of that area The proximal edge of the channel retractor is preferably tapered to gently separate skin away from the incision site. The proximal edge may also consist of a flange from which the retractor hollow surgical access chamber is extruded. The lower surface of the flange is adapted to function as a capture perimeter, resting on the surface of a patient and thereby preventing skin and tissue intrusion around the sides of the upper portion of the retractor.

FIGS. 1-5

In one embodiment, as represented by FIGS. 1 through 5, the surgical access assembly is a retractor 10 in the form of an oblong rectangular shape, into which an oblong rectangular shaped wedge introducer 12 may be inserted for surgical access to the anterior spinal column. When viewed from the top as in FIG. 4, through the neck of a supine patient, the cross-section of the surgical access assembly is generally oblong, that is, said surgical access assembly is generally rectangular in cross-section, rounded at the corners, but with parallel sides extending parallel to each other from the proximal end to the distal end as seen in FIG. 1.

Hollow retractor 10 may be flared at a proximal end 26 adjacent to the skin incision region as seen in FIG. 3. The fixation shafts 22 are imbedded within the walls of the retractor 10 and have rounded manipulable handles 20 so that they can be screwed into placed within vertebral bone.

When the introducer element 12, having a length greater than the length of the hollow access channel 28, is introduced into the access channel, it protrudes from the base of the retractor. Said introducer element's distal end 32 is smooth and rounded. The smoothness and roundness of the introducer element's distal end work to spread apart the skin and other soft tissues. When the apparatus is introduced into the patient, a fixation means such as a screw 18, is placed in the fixation shaft 22, and affixed to vertebrae 34 or other structure. The introducer is removed, thereby leaving the retractor 10 and the hollow access channel 28. The channel provides access for the surgeon and instruments to the target area and accompanying tissues and structures.

The surgical access assembly, in this embodiment and optionally others, therefore includes an interleaved combination of an oblong cross-sectional open sleeve hollow retractor 10 and a tipped wedge introducer 12 such that the introducer is introduced into an area adjacent to the hollow sleeve, the distal tip of the wedge introducer extending beyond the distal end of the hollow retractor so that the wedge introducer traverses the tissue ahead of the distal end of the hollow retractor and thereby guides the hollow retractor into place adjacent to the vertebrae. The tipped wedge introducer 12, in this embodiment and optionally others, has an exterior surface corresponding to an interior surface of the hollow sleeve and the closed end tipped wedge introducer may have a diameter with an oblong cross-section approximating the oblong shape of the open sleeve of the retractor.

With respect to the drawing figures, FIG. 1 shows retractor 10 with introducer 12 prior to insertion of introducer 12 through access channel 28. The parallel walls 30 are sized and contoured to provide a close fit within access channel 28. The proximal side of the retractor 10 is flared or tapered 38 to keep the skin at the incision from slipping over the proximal end thereby occluding part of access channel 28. The wall thickness of the ends of retractor 10 is sufficient to accommodate fixation shafts 22 that guide a fixation means, such as screws 18, which are used to fixate retractor 10 to vertebrae. Screw heads 20 have a smooth top with knurled sides so that they can be easily forced down and turned manually so that pointed screw ends 24 can engage and penetrate a vertebra. Introducer 12 has a gradually rounded end 32 designed to gently separate the tissues and other soft features above the vertebrae.

FIG. 2 shows a side cross-section of retractor 10 over a schematic representation of cervical vertebrae. Screws 18 are entering vertebrae C3 and C5 for anchoring. The discs 36 between C3 and C4 and also C4 and C5 are accessible through access channel 28.

FIG. 3 is an end view cross-section of retractor 10 showing that side walls have a thinner cross-section than the end walls shown in FIG. 2 which contain holes to accommodate screws 18.

FIG. 4 is a top view of retractor 10 showing access channel 28 that is an oblong through-hole.

Prior to insertion through an incision, introducer 12 is placed within access channel 28 of retractor 10 as shown in the side elevation of FIG. 5. The resulting assembly presents a smoothly contoured distal end with end 32 of introducer 12 continuing the rounded wall 32 bottom edge in an unbroken contour. The assembly is inserted through the incision and then fixed via screws 18 or by alternate means.

FIGS. 6-19

Additional Embodiments

In another embodiment, as represented by FIGS. 6 through 19, the surgical access assembly comprises a retractor 50, the body of said retractor in the form of an oblong rectangular shape as seen in FIG. 8. The surgical access assembly further comprises the hollow surgical access channel 68 of the retractor 50 into which an oblong rectangular shaped wedge introducer 52 may be inserted for surgical access to the anterior spinal column. The top portion of said introducer 52 has a thumb-grip 56 for grasping by the surgeon or by other grasping means as seen in FIGS. 1 and 12.

Figure 7:
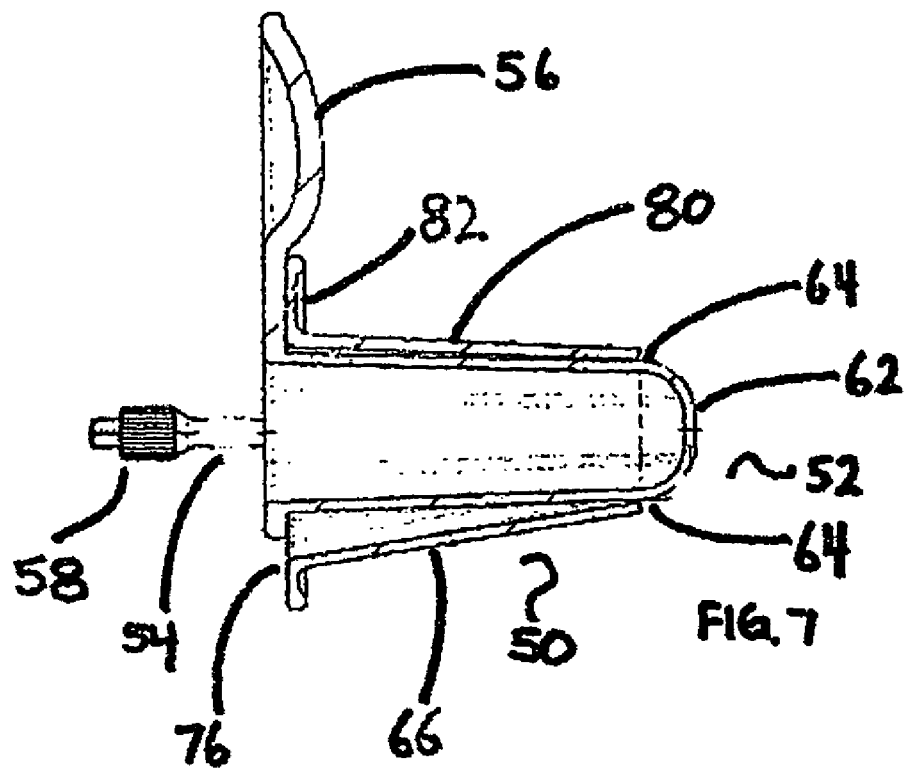

When viewed from the top as in FIG. 6, through the neck of a supine patient, the cross-section of the surgical access assembly is generally oblong, that is, said surgical access assembly is generally rectangular in cross-section exclusive of the thumb-grip and rounded at the corners. The introducer 52 has walls 78 that run parallel to each other along the length of the introducer from the distal end 62 to the proximal end. The retractor outer and inner walls 80, proximate to the thumb grip 56, run parallel to the introducer wall 52 adjacent the retractor wall 80 proximate to the thumb grip 56 as seen in FIG. 7. The retractor inner wall opposite the thumb grip 56 runs parallel to the introducer wall 52 adjacent the retractor inner wall opposite the thumb grip 56 as also seen in FIG. 7. Finally, the retractor outer wall 66 opposite the thumb grip 56 tapers gradually from the top of the retractor device to the distal end of the retractor device as seen in FIG. 7.

The hollow retractor 50, as seen in FIG. 17, has a table base 76 (not shown) from which the access channel 68 is extruded. At the underside of table base 76, the capture perimeter 82 is adapted to provide a surface that prevents tissue creep around the top of the retractor device. The holes of the introducer 74, as seen in FIGS. 8, 10 and 11, allow a fixation device such as a screw 54, again as seen in FIG. 8, to pass through and into the vertical fixation shaft 72 of the retractor 50. The retractor 50, as seen in FIGS. 9, 17, and 19 has shafts 72 that are imbedded within the wails of the retractor 50. The screws 54, a possible fixation device, can be screwed into placed at their tips 60 within vertebral bone.

When the introducer element 52, having a length greater than the length of the hollow access channel 68, is introduced into the access channel, it protrudes from the base of the retractor as seen clearly in FIG. 7. Said protruding introducer element's distal end 62 is smooth and rounded. The introducer elements protruding distal end 62 terminates at the boundary, junction point 64. The resulting assembly presents a smoothly contoured distal end with end 62 of the introducer 52 continuing the rounded wall bottom edge, junction point 64 in an unbroken contour. The smoothness and roundness of the introducer element's distal end 62 works to spread apart the skin and other soft tissues.

When the apparatus is introduced into the patient, fixation means such as a screw 54 are placed through the introducer entryways 74 into the vertical fixation shafts 72 and advanced until joined with bone or other tissue. The introducer 52 is removed, leaving the retractor 50 and the hollow access channel 68. Access is thereby provided for the surgeon to the target area and accompanying tissues and structures.

The surgical access assembly, in this embodiment and optionally others, therefore includes an interleaved combination of an oblong cross-sectional open sleeve hollow retractor 50 and a tipped wedge introducer 52 such that the introducer is introduced into an area adjacent to the hollow sleeve, the distal tip of the wedge introducer extending beyond the distal end of the hollow retractor so that the wedge introducer traverses the tissue ahead of the distal end of the hollow retractor and thereby guides the hollow retractor into place adjacent to the vertebrae.

The tipped wedge introducer, in this embodiment and optionally others, has an exterior surface corresponding to an interior surface of the hollow sleeve and the closed end tipped wedge introducer may have a diameter with an oblong cross-section approximating the oblong shape of the open sleeve of the retractor. The introducer element 52 may have a hollow chamber 70 terminated with a wall forming the distal end's protruding element 62. Alternatively, the introducer element may be a solid with the exception of the vertical fixation shaft entryways 74.

With respect to the figures, FIG. 6 is a top plan view of the introducer 52 and retractor 50 with the introducer 52 positioned within the access channel 68 (not visible) prior to insertion at the surgical site. A fixation means, here a screw 54, is inserted into the vertical fixation shafts 72 (not visible) of the retractor 50 through the vertical fixation shaft entryways 74 of the introducer 52. The screw head 58 is visible. Gripping means, here a thumb-grip 56, is visible as tongue-like extension of the introducer 52. The flange surface 76 of the retractor forms an oblong cross-section that would rest above the incision site.

FIG. 7 is a side cross-section view of the introducer 52 with the introducer positioned within the hollow surgical access channel 68 of the retractor 50 prior to insertion at the surgical site. Screw head 58 and screw 54 are visible. The gripping means, here a thumb-grip 56 with a spoon-shaped cross section for better handling by a surgeon or other gripping device, is shown extending outward from the introducer 52 over the flange 76 of the retractor 50 along the side opposite tapered wall 66. The junction point of the retractor 50 and the introducer's protruding distal end 62 exists at point 64. The surface from the distal end 62 to the junction point 64 and onward to the tapered wall 66, parallel wall 80, and intervening surface walls of the retractor, is a continuous unbroken contour.

FIG. 8 is a perspective view of the introducer 52 positioned over the retractor 50 of this invention with a possible fixture means, namely screws 54, positioned over the vertical fixation shafts 72. The screws, their tips 60 and their heads 58, pass through entryway 74, into the vertical fixation shafts 72. The thumb-grip gripping means 56 is seen extending outward from the top-portion of introducer 52 in a tongue-like manner. The introducer walls 78, parallel at opposite sides from each other, are also visualized. The introducer walls 78, on the same side as the vertical fixation shafts 72, are parallel to each other but contoured to fit snugly alongside the fixation shafts of the retractor. The introducer's distal end 62 is smooth and rounded and is visualized. Junction point 64 is also shown. The introducer 52 is hollow in this embodiment, helping provide visualization of tissue and structure beneath it when the introducer material is transparent, allowing viewing through the distal end surface. Finally, the hollow surgical access channel 68 is seen prior to insertion of the introducer.

FIG. 9 is a side cross-section view of the introducer 52 with the introducer positioned within the hollow surgical working of the retractor 50 and access channel 68 (not visible) and a possible fixation means, namely screws 54, their tips 60 and their heads 58, positioned partially within the vertical fixation shafts and fully within the vertical fixation shafts. The snug fit of the introducer positioned within the retractor is apparent from this figure. Further, junction point 64 and the introducer's distal end 62 and its smooth, rounded contour are visualized.

FIG. 10 is a top plan view of the introducer 52 only. The tongue-like gripping means 56 is shown. Of note is the vertical fixation shaft entryway 74, which provides a passage for a fixating device such as screw or other device.

FIG. 11 is a perspective view of the introducer 52 only. The tongue-like gripping means 56 is shown with a depression for better gripping by a thumb or other device. Of note is the vertical fixation shaft entryway 74, which provides a passage for a fixating device such as a screw or other device. Also of note are the contoured introducer walls 78 and the distal end 62 that continues in a rounded, smooth manner to junction point 64.

FIG. 12 is a side cross-section view of the introducer 52 only. The indentation of gripping means 56 is clearly seen as well as the parallel nature of the walls 78 not parallel to the vertical fixation shafts of the retractor (not shown). The distal end 62 of the introducer 52 continues in a rounded, smooth manner to junction point 64.

FIG. 13 is a side view of the introducer 52 only, showing the distal end 62.

FIG. 14 is another side view, cross-section of the introducer 52 only, demonstrating the contour of a cross-section of the introducer 52, the parallel walls 78, and the distal nub 62. Further, the hollow, terminus barriered introducer chamber 70 is clearly shown.

FIG. 15 is a top plan view of the retractor 50 only. The flange surface 76 and the oblong architecture of the retractor is seen from this top-plan perspective. The fixation shafts 72 are placed at opposite ends of the retractor. The retractor 50 provides a hollow surgical access chamber 68.

FIG. 16 is a side cross-section view of the retractor 50 only. The flange surface 76 and the underside capture perimeter 82 of the retractor 50 extends to the extrusion point where the surgical access chamber 68 is formed by the surrounding walls, which include a straight wall 80 and a tapered wall 66, which results in a wedge-like shape for the retractor 50.

FIG. 17 is a perspective view of the retractor 50 only in which the capture perimeter 82 is shown from below. Vertical fixation shafts 72 are also shown as well as the surgical access chamber 68. This view demonstrates a possible contour for the outer walls of the retractor.

FIG. 18 is a top-plan view of the retractor 50 only and shows the surgical access chamber 68 as well as the flange surface 76. The contour of the portion of the retractor is partially visible and indicates the tapered wall 66.

FIG. 19 is a side cross-section view of the retractor 50 only. The surgical access chamber 68 as well as the flange surface 76 and the underlying capture perimeter 82 are again shown. The cross-section details the vertical fixation shafts 72. As can be seen, in one embodiment, the fixation shaft terminus can narrow to allow extrusion of a fixating device, such as a screw tip but not the entire screw, providing a support for affixing the retractor 50 into bone.

In an alternative conception of the above surgical access assembly, the introducer 52 vertical fixation shaft entryway 74 may be extruded into the vertical fixation shaft chamber 72 of the retractor 50. The resulting sleeve would be adapted to anchor the introducer 52 into the retractor 50. The fixation means, such as a screw 54, would still have access to the retractor's 50 vertical fixation shaft 72. The sleeve-like introducer chamber 128 as shown in FIG. 20 is representative.

FIGS. 20-22

Alternative Embodiments

In another exemplary and preferred alternative embodiment of the invention, the retractor element 106 is expandable such that a small assembly footprint may initially be inserted into the patient. In this embodiment, a protruding introducer element 104, having a length greater than the length of the hollow surgical access channel 116, thereby providing a protruding end 102, is introduced into the surgical access channel 116. Said introducer element's distal end 102 is smooth and rounded. The smoothness and roundness of the introducer element's distal end 102 works to spread apart the skin and other soft tissues. The introducer also has sleeved entryways 128 whereby screws or other fixation means and fixation means channels such as 120 may pass through. The sleeves 128 serve to anchor the retractor halves 108 and 110 into place until fixation of the retractor 106 into bone.

When the retractor 106 and inserted introducer 104 are introduced into an opening in a patient, fixation means such as a screw 118 are placed into the vertical fixation shafts 114 and advanced until joined with bone or other tissue. The introducer 104 is removed, leaving the retractor 106 and the hollow access channel 116. The retractor 106 may now be adjusted to expand in size, thereby pushing tissue and structure away from the center of the device, by, for example, a distractor device 124 affixed through the vertical fixation shafts 114 over the screw head 126 onto the screw head post 118 by a channel 120 on the distractor device 124. The distraction means 122 can be any means found in standard distractors such as by a screw-actuated guidepost which increases or decreases the distance between the fixation means channel 120. During expansion or contraction, inner retractor first half 108 slides past the outer retaining walls of the outer retractor second half 110. The inner retractor first half tip edge and outer retractor second half tip edge may be designed to include a clasping edge 112 such that over expansion is prevented.

Further, the introducer may incorporate gripping means such as a thumb-grip 130. Access is thereby provided for the surgeon to the target area and accompanying tissues and structures.

The surgical access assembly, in this embodiment and optionally others, therefore includes an interleaved combination of an oblong cross-sectional open sleeve hollow retractor of two pieces and a tipped wedge introducer such that the introducer is introduced into an area adjacent to the hollow sleeve, the distal tip of the wedge introducer extending beyond the distal end of the hollow retractor so that the wedge introducer traverses the tissue ahead of the distal end of the hollow retractor and thereby guides the hollow retractor into place adjacent to the vertebrae. The tipped wedge introducer, in this embodiment and optionally others, has an exterior surface corresponding to an interior surface of the hollow sleeve and the closed end tipped wedge introducer may have a diameter with an oblong cross-section approximating the oblong shape of the open sleeve of the retractor. Further, this surgical access assembly comprises a hollow retractor design capable of expansion or contraction along the axis intersecting the fixation shafts. The expansion or contraction functions to distract bone or other structure by transmitting the force of said expansion or contraction along the vertical fixation shafts, which are affixed in said bone or other structure. A minimal number of fixation means such as screws is thereby required to retract surrounding tissue and structure and distract attached bone or other structure.

With respect to the figures, FIG. 20 shows a perspective view of the apparatus. Distractor 124 is positioned over fixation means 126, here a screw, said fixation means positioned over the retractor's 106 first retractor half's 108 vertical fixation shaft 114 and over the retractor's 106 second retractor half's 110 vertical fixation shaft 114. Also shown is introducer 104 positioned over the hollow surgical access chamber 116. Distractor 124 has distraction means 122 such that when the distractor fixation means channel 120 is placed over fixating device 118 which are inside vertical fixation means shaft 114 and fixating device 118 is affixed to bone or other structure, said means can cause distraction by transmitting an expanding or contracting force from means 122 to 120 to 118 to retractor first half 108 and retractor second half 110 and the affixed underlying tissue or structure. Also seen in this view is the distal end 102 of the introducer, the gripping means 130, here a thumb-grip, of the introducer 106, and the introducer sleeves 128 through which fixating means 118 pass. Lastly, clasping edge 112, flange surface 136, and screw ring 134 are shown. The flange surface 136 is substantially the same size on the retractor first half 108 as it is on retractor second half 110, thus the distance from the channel 120 to the outward edge of 136 is nearly equivalent on either retractor half, thereby resulting in top-view similar to FIG. 4. The capture perimeter 132 lying on the underside of 136 is not visible but is similar in form and function as 82 in FIG. 17.

FIG. 21 shows an expanded detail view of the distractor channel 120, the fixation means (screw) 118, the vertical fixation shaft 114, screw tip 126, and ring 134 in combination as in a typical use after the introducer (not shown) has been removed and the distractor engaged to the retractor. As can be seen, screw 118 is fully chambered within the fixation shaft of 114, its further ingress halted by screw ring's 134 contact with the terminus of the fixation shaft 114. Screw ring 134 serves to engage the retractor to the screw fixing the retractor into bone. Distraction chamber 120 is shown fully chambered within 114. As can also be seen, distraction chamber 120 snugly fits the perimeter of the screw ring 134 and therefore meets the terminus of the fixation shaft 114. Finally, screw tip 126 is seen protruding from below the fixation shaft 114.

FIG. 22 displays an expanded top view of the interlocking mechanism of smaller retractor first half 108 and larger retractor second half 110. The arrows indicate the range of motion of the retractor halves. The capture perimeter 132 and flange top 136 are not shown for clarity. A detail shows a possible clasping mechanism for the clasping edges 112. As the retractor is expanded, edges 112 meet and prevent further translation outward.

CONCLUSION AND SCOPE

In the foregoing descriptions, certain terms and visual depictions are used to illustrate the preferred embodiments. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended claims. Therefore, the present invention encompasses one or more surgical instrument assemblies providing access to spinal vertebrae and associated discs, through a transcutaneous incision, for a variety of reasons, such as to access a spinal surgical site, and provides means for distraction of affixed structures such as vertebrae.

The invention claimed is:

1. A surgical access assembly comprising:
a retractor having
a first half and a second half, said second half clasping said first half to form a closed perimeter of oblong cross-section,
said first half having
smooth outer walls having
substantially the shape of a "U" and
a gapless contour adapted to
distribute pressure evenly along said outer wall,
minimize localized retraction pressure, and
fit snugly within the inner walls of said second half and contoured to allow said inner walls of said second half to slide
past said outer walls of said first half,
smooth inner walls having substantially the shape of a "U" and said second half having
smooth outer walls having substantially the shape of a "U" and
a gapless contour adapted to distribute pressure evenly along said outer wall and to minimize localized retraction pressure,
smooth inner walls having substantially the shape of a "U" and
a gapless contour adapted to fit snugly outside the outer walls of said first half and contoured to allow said walls of said first half to slide past said walls of said second half,
said first half and said second half adapted to
receive a smooth and rounded introducer,
allow expansion or contraction of said retractor by the sliding of said first half past said second half and said second half past said first half and provide a hollow access chamber, said surgical access assembly adapted to allow said surgical access chamber to be of variable size; and fixation shafts adapted to receive a fixating device;

said smooth and rounded introducer having
- a continuous perimeter with no sharp edges, adapted with a contour and size to fit within said hollow access channel, and
- a length such that the distal end of the introducer protrudes past the distal end of said hollow access channel when inserted into said retractor thereby providing a protruding nub, and said nub forming a smooth contour; and a distractor adapted to affix to said retractor and further adapted to allow access of said fixating device into said fixating shaft while said distractor is affixed onto said retractor.

2. The surgical access assembly of claim 1 further comprising a distractor adapted to affix to said fixating device.

3. The surgical access assembly of claim 1 further comprising a distractor adapted to affix to said retractor.

4. The surgical access assembly of claim 1 in which said distractor is adapted to provide expansion and contraction of said retractor.

5. The surgical access assembly of claim 1 in which said introducer is adapted to secure said first half and said second half together until said retractor is affixed to structure within a patient.

6. The surgical access assembly of claim 1 comprising fixation shafts placed at opposite sides of said retractor.

7. The surgical access assembly of claim 6 in which said fixating devices are screws.

8. The surgical access assembly of claim 1, wherein said retractor has a flange forming the upper perimeter of said retractor, adapted to prevent tissue creep and extrusion over the top of said retractor.

9. The surgical access assembly of claim 1, wherein said retractor comprises tapered forward edges adapted to prevent tissue creep and extrusion over the top of said retractor.

10. The surgical access assembly of claim 1, wherein said introducer is hollow.

11. The surgical access assembly of claim 1, wherein said surgical access assembly further comprises a grip on said introducer adapted for gripping by a surgeon or gripping device.

12. The surgical access assembly of claim 11, wherein said grip is a thumb-grip.

13. The surgical access assembly of claim 1 in which said surgical access assembly is made from materials that are lightweight and biocompatible.

14. The surgical access assembly of claim 1 in which said surgical access assembly is made from materials that are lightweight, biocompatible, and transparent.

15. The surgical access assembly of claim 1 in which said surgical access assembly is made from materials that are biocompatible and having a shape memory.

16. The surgical access assembly of claim 1, wherein said introducer has hollow sleeves aligned for entry into said fixation shaft, adapted to allow fixating devices to pass through.

17. The surgical access assembly of claim 1 in which said first half and said second half are adapted to provide a clasping edge to prevent over-expansion during expansion of the retractor.

18. A surgical access assembly comprising:
a retractor having
- a first half and a second half, said second half clasping said first half to form a closed perimeter of oblong cross-section,
- said first half having
  - smooth outer walls having substantially the shape of a "U" and
  - a gapless contour adapted to
    - distribute pressure evenly along said outer wall,
    - minimize localized retraction pressure, and
    - fit snugly within the inner walls of said second half and contoured to allow said inner walls of said second half to slide past said outer walls of said first half,
  - smooth inner walls having substantially the shape of a "U" and said second half having
  - smooth outer walls having substantially the shape of a "U" and a gapless contour adapted to distribute pressure evenly along said outer wall and to minimize localized retraction pressure,
  - smooth inner walls having substantially the shape of a "U" and a gapless contour adapted to fit snugly outside the outer walls of said first half and contoured to allow said walls of said first half to slide past said walls of said second half,
- said first half and said second half adapted to
  - receive a smooth and rounded introducer,
  - allow expansion or contraction of said retractor by the sliding of said first half past said second half and said second half past said first half and
  - provide a hollow access chamber, said surgical access assembly adapted to allow said surgical access chamber to be of variable size; and fixation shafts adapted to receive respective fixating devices;

said smooth and rounded introducer having
- a continuous perimeter with no sharp edges, adapted with a contour and size to fit within said hollow access channel, and
- a length such that the distal end of the introducer protrudes past the distal end of said hollow access channel when inserted into said retractor thereby providing a protruding nub, and said nub forming a smooth contour; and hollow sleeves aligned for entry into said fixation shafts, adapted to allow the fixating devices to pass through.

19. The surgical access assembly of claim 18 further comprising a distractor adapted to affix to said fixating device or said retractor, the distractor being adapted to provide expansion and contraction of said retractor.

20. The surgical access assembly of claim 18 in which said introducer is adapted to secure said first half and said second half together until said retractor is affixed to structure within a patient.

21. The surgical access assembly of claim 18, wherein said retractor has a flange forming the upper perimeter of said retractor or tapered forward edges adapted to prevent tissue creep and extrusion over the top of said retractor.

22. The surgical access assembly of claim 18, wherein said introducer is hollow.

23. The surgical access assembly of claim 18 in which said first half and said second half are adapted to provide a clasping edge to prevent over-expansion during expansion of the retractor.

24. A surgical access assembly comprising:
a retractor having
- a first half and a second half, said second half clasping said first half to form a closed perimeter of oblong cross-section,
- said first half having
  - smooth outer walls having
  - substantially the shape of a "U" and
  - a gapless contour adapted to
    - distribute pressure evenly along said outer wall,
    - minimize localized retraction pressure, and
    - fit snugly within the inner walls of said second half and contoured to allow said inner walls of said second half to slide past said outer walls of said first half,
  - smooth inner walls having substantially the shape of a "U" and said second half having
  - smooth outer walls having substantially the shape of a "U" and
  - a gapless contour adapted to distribute pressure evenly along said outer wall and to minimize localized retraction pressure,
  - smooth inner walls having substantially the shape of a "U" and
  - a gapless contour adapted to fit snugly outside the outer walls of said first half and contoured to allow said walls of said first half to slide past said walls of said second half,
- said first half and said second half adapted to
  - receive a smooth and rounded introducer,
  - allow expansion or contraction of said retractor by the sliding of said first half past said second half and said second half past said first half and
  - provide a hollow access chamber, said surgical access assembly adapted to allow said surgical access chamber to be of variable size; and
- fixation shafts adapted to receive a fixating device;

said smooth and rounded introducer having
- a continuous perimeter with no sharp edges, adapted with a contour and size to fit within said hollow access channel, and
- a length such that the distal end of the introducer protrudes past the distal end of said hollow access channel when inserted into said retractor thereby providing a protruding nub, and said nub forming a smooth contour, and
- wherein said introducer secures said first half and said second half immovably together until said retractor is adapted to be affixed to structure within a patient.

* * * * *